(12) United States Patent
Haubert et al.

(10) Patent No.: US 7,919,049 B2
(45) Date of Patent: *Apr. 5, 2011

(54) BUFFY COAT SEPARATOR FLOAT SYSTEM AND METHOD

(75) Inventors: Thomas Haubert, Columbus, OH (US); Vince Contini, Powell, OH (US); Steve Grimes, Westerville, OH (US); Randy Jones, Delaware, OH (US); Stephen C. Wardlaw, Lyme, CT (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/614,602

(22) Filed: Nov. 9, 2009

(65) Prior Publication Data

US 2010/0074803 A1    Mar. 25, 2010

Related U.S. Application Data

(63) Continuation of application No. 12/029,289, filed on Feb. 11, 2008, now Pat. No. 7,629,176, which is a continuation of application No. 11/609,186, filed on Dec. 11, 2006, now Pat. No. 7,358,095, which is a continuation of application No. 10/263,974, filed on Oct. 3, 2002, now Pat. No. 7,220,593.

(51) Int. Cl.
   *G01N 1/18*      (2006.01)
   *G01N 33/48*     (2006.01)

(52) U.S. Cl. ............. 422/101; 422/72; 422/73; 436/63; 436/174; 436/177; 210/782

(58) Field of Classification Search .................... 436/43, 436/45, 63, 174, 177; 422/58, 59, 60, 72, 422/73, 101, 102; 435/2, 288.2; 210/782, 210/789

See application file for complete search history.

(56) References Cited

U.S. PATENT DOCUMENTS 3,814,248 A    6/1974    Lawhead
(Continued)

FOREIGN PATENT DOCUMENTS

WO    WO 02/078848 A2    10/2002
(Continued)

OTHER PUBLICATIONS

Supplementary European Search Report, Application No. EP 03 79 9392, Date of completion of the search Nov. 24, 2009, 3 pages.

*Primary Examiner* — Maureen M Wallenhorst
(74) *Attorney, Agent, or Firm* — Richard M. Klein; Fay Sharpe LLP

(57) ABSTRACT

A tube and float system for use in separation and axial expansion of the buffy coat includes a transparent or semi-transparent, flexible sample tube and a rigid separator float having a specific gravity intermediate that of red blood cells and plasma. The float includes a main body portion of reduced diameter to provide a clearance gap between the inner wall of the sample tube and the float. One or more protrusions on the main body portion serve to support the flexible tube. During centrifugation, the centrifugal force causes the diameter of the flexible tube to expand and permit density-based axial movement of the float in the tube. The float further includes a pressure relief system to alleviate pressure build up in the trapped red blood cell blood fraction below the float, thereby preventing red blood cells from being forced into the annular gap containing the buffy coat layers.

20 Claims, 5 Drawing Sheets

U.S. PATENT DOCUMENTS

| | | |
|---|---|---|
| 3,890,237 A | 6/1975 | Welch |
| 4,082,085 A | 4/1978 | Wardlaw et al. |
| 4,091,659 A | 5/1978 | Massey, III et al. |
| 4,154,690 A | 5/1979 | Ballies |
| 4,717,660 A | 1/1988 | Schulte |
| 4,853,137 A | 8/1989 | Ersson |
| 4,917,801 A | 4/1990 | Luderer et al. |
| 4,921,618 A | 5/1990 | Hamlin |
| 4,953,975 A | 9/1990 | Levine et al. |
| 5,086,784 A | 2/1992 | Levine et al. |
| 5,251,474 A | 10/1993 | Wardlaw et al. |
| 5,266,199 A | 11/1993 | Tsukagoshi et al. |
| 5,282,981 A | 2/1994 | Adams et al. |
| 5,354,483 A | 10/1994 | Furse |
| 5,393,674 A | 2/1995 | Levine et al. |
| 5,776,710 A | 7/1998 | Levine et al. |
| 6,409,528 B1 | 6/2002 | Bodnar |
| 6,516,953 B1 | 2/2003 | DiCesare et al. |
| 7,074,577 B2 * | 7/2006 | Haubert et al. ............... 435/7.24 |
| 7,220,593 B2 * | 5/2007 | Haubert et al. ............... 436/177 |
| 7,329,534 B2 * | 2/2008 | Haubert et al. ............ 435/287.1 |
| 7,358,095 B2 * | 4/2008 | Haubert et al. ............... 436/177 |
| 7,629,176 B2 * | 12/2009 | Haubert et al. ............... 436/177 |
| 2003/0205538 A1 | 11/2003 | Dorian et al. |
| 2004/0067536 A1 | 4/2004 | Haubert et al. |

FOREIGN PATENT DOCUMENTS

| | | |
|---|---|---|
| WO | WO 02/078848 A3 | 10/2002 |

* cited by examiner

BUFFY COAT SEPARATOR FLOAT SYSTEM AND METHOD

CROSS-REFERENCE TO RELATED APPLICATIONS

This application is a continuation of U.S. patent application Ser. No. 12/029,289, filed Feb. 11, 2008, now U.S. Pat. No. 7,629,176, which is a continuation of U.S. patent application Ser. No. 11/609,186, filed Dec. 11, 2006, now U.S. Pat. No. 7,358,095, which in turn is a continuation of U.S. patent application Ser. No. 10/263,974, filed Oct. 3, 2002, now U.S. Pat. No. 7,220,593, all of which are incorporated herein by reference in their entireties.

FIELD OF THE INVENTION

The present invention relates generally to density-based fluid separation and, in particular, to an improved sample tube and float design for the separation and axial expansion of constituent fluid components layered by centrifugation, and a method employing the same. The present invention finds particular application in blood separation and axial expansion of the buffy coat layers, and will be described with particular reference thereto. However, it will be recognized that the present invention is also amenable to other like applications.

BACKGROUND OF THE INVENTION

Quantitative Buffy Coat (QBC) analysis is routinely performed in clinical laboratories for the evaluation of whole blood. QBC analysis techniques generally employ centrifugation of capillary tubes containing anticoagulated whole blood, to separate the blood into six distinct layers: (1) packed red cells, (2) reticulocytes, (3) granulocytes, (4) lymphocytes/monocytes, (5) platelets, and (6) plasma. Based on examination of the tube, the length or height of essentially each layer is determined and converted into a cell count, thus allowing quantitative measurement of each layer. The length can be measured with a manual reading device, i.e., a magnification eyepiece and a manual pointing device, or photometrically by an automated optical scanning device that finds the layers by measuring light transmittance and fluorescence along the length of the tube. A series of commonly used QBC instruments are manufactured by Becton-Dickinson and Company of Franklin Lakes, N.J.

Since the buffy coat layers are very small, the buffy coat is often expanded in the tube for more accurate visual or optical measurement by placing a plastic cylinder, or float, into the tube. The float has a density which is less than that of red blood cells (1.090 g/ml) and greater than that of plasma (1.028 g/ml) and occupies nearly all of the cross-sectional area of the tube. The volume-occupying float, therefore, generally rests on the packed red blood cell layer and greatly expands the axial length of the buffy coat layers in the tube for analysis.

There exists a need in the art for an improved sample tube and float system and method for separating blood and/or identifying circulating cancer and/or other rare cells, organisms or particulates or objects (i.e., stem cells, cell fragments, virally-infected cells, trypanosomes, etc.) in the buffy coat or other layers in a blood sample. However, the number of cells expected to be typically present in the buffy coat is very low relative to the volume of blood, for example, in the range of about 1-100 cells per millimeter of blood, thus making the measurement difficult, particularly with the very small sample sizes employed with the conventional QBC capillary tubes and floats.

The present invention contemplates a new and improved blood separation assembly and method that overcome the above-referenced problems and others.

SUMMARY OF THE INVENTION

In a first aspect of the present invention, an apparatus for separation and analysis of a target analyte in sample of anticoagulated whole blood is provided. The apparatus includes a transparent or semi-transparent, flexible tube for holding the sample and an elongate, rigid, volume-occupying float having a specific gravity intermediate that of red blood cells and plasma. The float comprises a main body portion spacedly surrounded by the inner peripheral surface of the sidewall of the tube to form an annular volume therebetween. One or more support members protrude from the main body portion to engage and support the sidewall. An internal passage extends axially through the main body portion of the float. The sidewall of the tube is resiliently radially expandable in response to centrifugal force so as to permit axial movement of the float in the tube and fluid flow therearound during centrifugation. The internal passage is present to prevent excessive, disruptive fluid flow through the separated buffy coat layers caused by the collapse of the outer wall of the sample tube to form the analysis area during the deceleration period of centrifugation.

In a second aspect, a method of separating and axially expanding buffy coat constituents in a blood sample comprises introducing the blood sample into a flexible sample tube having an elongate side wall with an inner peripheral surface. An elongate, rigid volume-occupying float, which has a specific gravity intermediate that of red blood cells and plasma, is introduced into the flexible sample tube. The float comprises a main body portion spacedly surrounded by the inner peripheral surface of the sidewall of the tube to form an annular volume therebetween. One or more support members protrude from the main body portion of the float to engage and support the sidewall and an internal passage extends axially through the main body portion. The sample is centrifuged to effect a density-based separation of the blood sample into discrete layers at a rotational speed that causes a resilient radial expansion of the tube sidewall to a diameter that is sufficiently large to permit axial movement of the float in the tube. The float moves into axial alignment with at least the buffy coat layers of the blood sample in response to the centrifugal force and, thereafter, the rotational speed is reduced to cause the tube sidewall inner surface to capture the float.

In a third aspect, a volume occupying separator float is provided. The float is adapted for use with an associated sample tube and comprises a rigid main body portion and one or more rigid tube support members extending radially outwardly from the main body portion. The tube support members are sized to engage an inner wall of the sample tube and configured to maintain a clearance gap between the main body portion and the inner wall of the sample tube. The float further comprises means for alleviating excessive flow through the expanded cell layers present in the clearance gap during centrifugation.

In a fourth aspect, a method for detecting circulating epithelial cancer cells in an anticoagulated whole blood sample comprises combining the blood sample with one or more epithelial cell epitope-specific labeling agents so as to differentiate epithelial cancer cells from other cells in the blood sample. The blood sample is introduced into a transparent sample tube comprising a flexible sidewall having an inner peripheral surface and a volume-occupying separator float is inserted into the sample tube. The separator float comprises a rigid main body portion having a cross-sectional diameter less than an inner diameter of the sample tube and one or more rigid tube support members extending radially outwardly from the main body portion. The support members are sized to engage an inner wall of the sample tube and are configured to maintain a clearance gap between the main body portion and the inner wall. The separator float further comprises a pressure relief system for automatically relieving any pressure differential across opposite axial ends of the float as a result of centrifuging. The blood sample and separator float are centrifuged to effect centrifugally motivated localization of any epithelial cancer cells present in the blood sample within the clearance gap. After centrifuging, the blood sample is examined for the presence of epithelial cancer cells contained in the clearance gap, i.e., the analysis area.

In a still additional aspect, the compressibility and/or rigidity of the flexible sample tube and rigid float can be reversed. In this aspect, the float is designed to shrink in diameter at the higher pressures and moves freely within a rigid, or optionally, semi-rigid tube. The use of a compressible float allows for usage of transparent glass tubes, which, in some instances, exhibit enhanced optical properties over polymeric tubes. Furthermore, this aspect generally reduces the tolerance requirements for the glass tubes (since the float would expand up against the tube wall after the pressure decreases), and a full range of float designs is possible.

In another aspect, the step of centrifugation is not required. In such an aspect, the application of pressure alone to the inside of the tube, or simply the expansion of the tube (or the compression of the float) is required. For example, such pressure can be produced through the use of a vacuum source on the outside of the tube. Such an application also allows for the top of the sample tube to be kept open and easily accessible. Additionally, the use of a vacuum source may be easier to implement in some situations than the application of a centrifugal force.

Additionally, any method of tubular expansion/contraction (or float compression) such as mechanical, electrical, magnetic, etc., can be implemented. Once the tube is expanded (or the float is compressed), the float will move to the proper location due to buoyancy forces created by the density variations within the sample.

In a further aspect, the float comprises a part of a flexible collection tube system or assembly. In this aspect, it is not necessary to transfer the sample from a collection container to an analysis tube. The blood or sample fluid can be collected immediately and then tested. Such a system is somewhat faster, and also safer from a biohazard standpoint. For example, this system is desirable in very contagious situations (i.e. Ebola virus, HIV, etc.) where any type of exposure of the blood must be minimized.

One advantage of the present invention is found in a blood separating apparatus that can separate the entire buffy coat of a relatively large blood sample from the rest of the blood volume.

Another advantage of the invention resides in the fact that the buffy coat layers can be made available for visualization or imaging in one simple operation, i.e., centrifugation.

Still another advantage of the invention resides in enhanced buffy coat separation, retention, and, if desired, removal from the sample tube for further processing.

Another advantage of the invention resides in that reduced centrifugation speeds can be used to spin down the blood sample, thereby reducing possible tube failures.

Still another advantage is found in that the tube can be supported for improved imaging of the sample, and a more repeatable depth for imaging may be provided.

Still further advantages of the present invention reside in its relatively simple construction, ease of manufacture, and low cost.

Another advantage resides in that pressure beneath the float is automatically alleviated, thereby reducing contamination of the separated buffy coat by intruding red blood cells.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings, in which like reference numerals denote like components throughout the several views, are only for purposes of illustrating preferred embodiments and are not to be construed as limiting the invention.

DETAILED DESCRIPTION OF THE PREFERRED EMBODIMENTS

Figure 1:
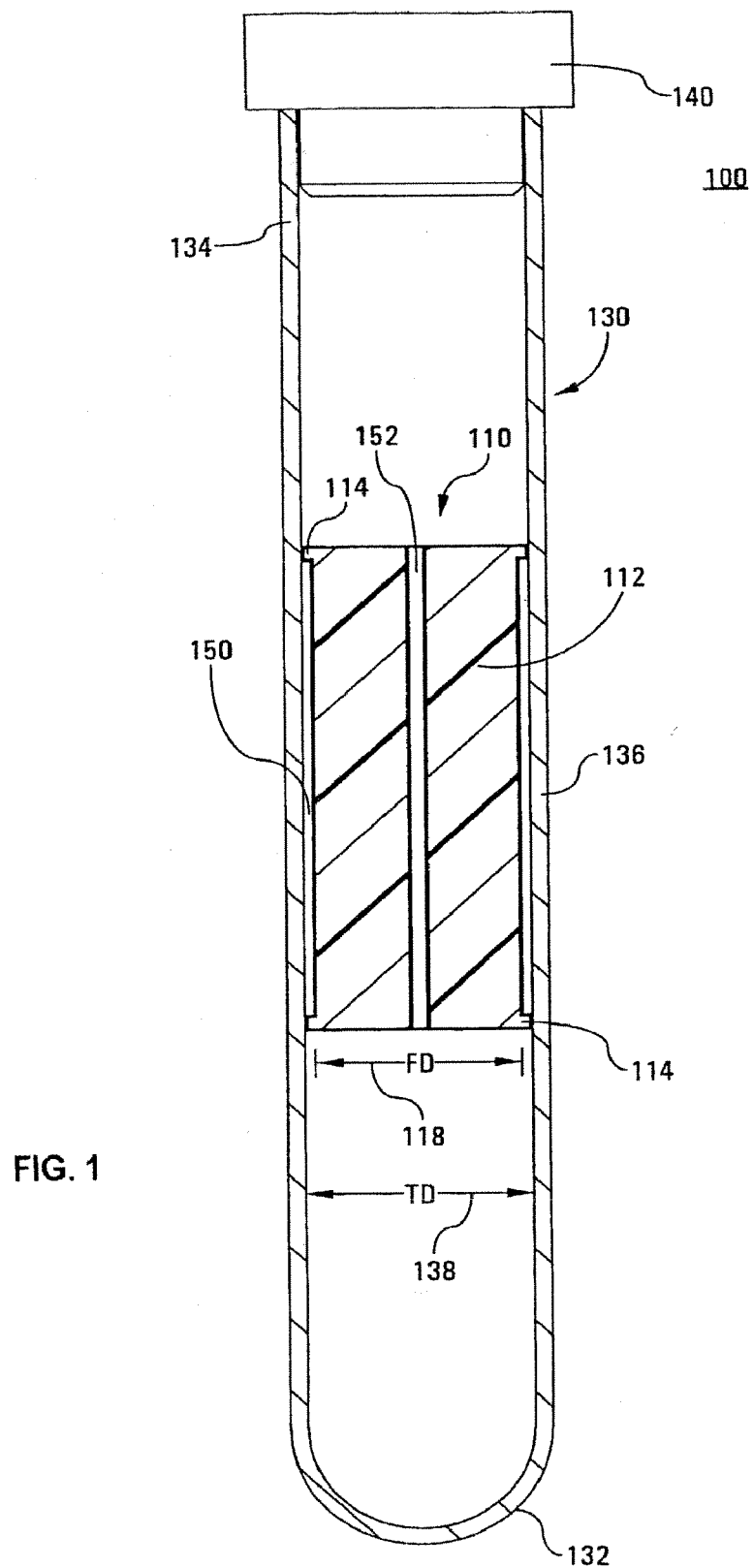
FIG. 1 is a sectional view of a sample tube containing a generally spool-shaped separator float with a central bore according to an exemplary embodiment of the invention.
Figure 2:
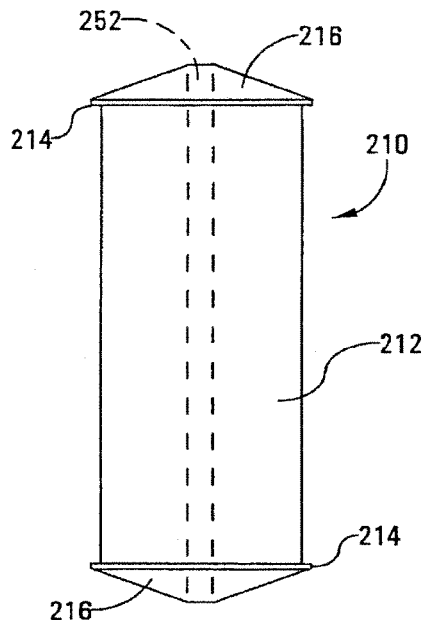
FIG. 2 is an elevational view of a separator float having generally conical ends according to another exemplary embodiment of the invention.

Turning now to the drawings, wherein the showings are for purposes of illustrating the preferred embodiments of the invention only and not for limiting the same, FIG. 1 shows a blood separation tube and float assembly 100, including a sample tube 130 having a separator float or bobber 110 of the invention therein.

The sample tube 130 is generally cylindrical in the depicted embodiment, although tubes having polygonal and other geometrical cross-sectional shapes are also contemplated. The sample tube 130 includes a first, closed end 132 and a second open end 134 receiving a stopper or cap 140. Other closure means are also contemplated, such as parafilm or the like. In alternative embodiments, not shown, the sample tube may be open at each end, with each end receiving an appropriate closure device.

Although the tube is depicted as generally cylindrical, the tube 130 may be minimally tapered, slightly enlarging toward the open end 134, particularly when manufactured by an injection molding process. This taper or draft angle is generally desirable for ease of removal of the tube from the injection-molding tool.

The tube 130 is formed of a transparent or semi-transparent material and the sidewall 136 of the tube 130 is sufficiently flexible or deformable such that it expands in the radial direction during centrifugation, e.g., due to the resultant hydrostatic pressure of the sample under centrifugal load. As the centrifugal force is removed, the tube sidewall 136 substantially returns to its original size and shape.

The tube may be formed of any transparent or semi-transparent, flexible material (organic and inorganic), such as polystyrene, polycarbonate, styrene-butadiene-styrene ("SBS"), styrene/butadiene copolymer (such as "K-Resin®" available from Phillips 66 Co., Bartlesville, Okla.), etc. Preferably, the tube material is transparent. However, the tube does not necessarily have to be clear, as long as the receiving instrument that is looking for the cells or items of interest in the sample specimen can "see" or detect those items in the tube. For example, items of very low level of radioactivity that can't be detected in a bulk sample, can be detected through a non-clear or semi-transparent wall after it is separated by the process of the present invention and trapped near the wall by the float 110 as described in more detail below.

In a preferred embodiment, the tube 130 is sized to accommodate the float 110 plus at least about five milliliters of blood or sample fluid, more preferably at least about eight milliliters of blood or fluid, and most preferably at least about ten milliliters of blood or fluid. In an especially preferred embodiment, the tube 130 has an inner diameter 138 of about 1.5 cm and accommodates at least about ten milliliters of blood in addition to the float 110.

The float 110 includes a main body portion 112 and two sealing rings or flanges 114, disposed at opposite axial ends of the float 110. The float 110 is formed of one or more generally rigid organic or inorganic materials, preferably a rigid plastic material, such as polystyrene, acrylonitrile butadiene styrene (ABS) copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides (aramids), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, and so forth, and most preferably polystyrene, polycarbonate, polypropylene, acrylonitrile butadiene-styrene copolymer ("ABS") and others.

In this regard, one of the objectives of the present invention is to avoid the use of materials and/or additives that interfere with the detection or scanning method. For example, if fluorescence is utilized for detection purposes, the material utilized to construct the float 110 must not have much "background" fluorescence at the wavelength of interest.

The main body portion 112 and the sealing rings or support members 114 of the float 110 are sized to have an outer diameter 118 which is less than the inner diameter 138 of the sample tube 130, under pressure or centrifugation. The main body portion 112 of the float 110 is also less than the sealing or support rings 114, thereby defining an annular channel or gap 150 between the float 110 and the sidewall 136 of the tube 130. The main body portion occupies much of the cross-sectional area of the tube, the annular gap 150 being large enough to contain the cellular components of the buffy coat layers and associated target cells when the tube is the non-flexed state. Preferably, the dimensions 118 and 138 are such that the annular gap 150 has a radial thickness ranging from about 25-250 microns, most preferably about 50 microns.

A bore or channel 152 extends axially through the float 110. When the tube/float system is centrifuged, the tube expands, freeing the float in the blood sample. As centrifugation is slowed, the float is captured by the wall 136 of the tube as it returns to its original diameter. As the tube continues to contract, pressure may build up in the blood fraction trapped below the float, primarily red blood cells. This pressure may cause red cells to be forced into the annular channel 150 containing the captured buffy coat layers, thus making imaging of the contents of the buffy coat more difficult. Alternatively, the collapse of the side wall of the sample tube during deceleration may produce excessive or disruptive fluid flow through the separated buffy coat layers. The bore 152 allows for any excessive fluid flow or any resultant pressure in the dense fractions trapped below the float 110 to be relieved. The excessive fluid flows into the bore 152, thus preventing degradation of the buffy coat sample.

Although the depicted embodiments illustrate the preferred configuration of a central, axially-aligned bore 152, it will be recognized that other configurations are contemplated so long as the bore extends completely from one end to the other. In the preferred embodiment, the bore 152 is centrally located and axially extending.

While in some instances the outer diameter 118 of the main body portion 112 of the float 110 may be less than the inner diameter 138 of the tube 130, this relationship is not required. This is because once the tube 130 is centrifuged (or pressurized), the tube 130 expands and the float 110 moves freely. Once the centrifugation (or pressurization) step is completed, the tube 130 constricts back down on the sealing rings or support ridges 114. The annular gap or channel 150 is then created, and sized by the height of the support ridges or sealing rings 114 (i.e., the depth of the "pool" is equal to the height of the support ridges 114, independent of what the tube diameter is/was).

In an especially preferred embodiment, the float dimensions are 3.5 cm tall×1.5 cm in diameter, with a main body portion sized to provide a 50-micron gap for capturing the buffy coat layers of the blood. Thus, the volume available for the capture of the buffy coat layer is approximately 0.08 milliliter. Since the entire buffy coat layer is generally less than about 0.5% of the total blood sample, the preferred float accommodates the entire quantity of buffy layer separated in an eight- to ten-milliliter sample of blood.

The sealing or support flanged ends 114 are sized to be roughly equal to, or slightly greater than, the inner diameter 138 of the tube. The float 110, being generally rigid, can also provide support to the flexible tube wall 136. Furthermore, the large diameter portions 114 provide a sealing function to maintain separation of the blood constituent layers. The seal formed between the large diameter regions 114 of the float and the wall 136 of the tube may be, but is not necessarily, a fluid-tight seal. As used herein, the term "seal" is also intended to encompass near-zero clearance or slight interference between the flanges 114 and the tube wall 136 providing a substantial seal, which is, in most cases, adequate for purposes of the invention.

The sealing rings 114 are most preferably continuous ridges, in which case the sample may be centrifuged at lower speeds and slumping of the separated layers is inhibited. However, in alternative embodiments, the ridges or sealing rings can be discontinuous or segmented bands having one or openings providing a fluid path in and out of the annular gap 150. The sealing rings or ridges 114 may be separately formed and attached to the main body portion 112. Preferably, however, the sealing ridges 114 and the main body portion 112 form a unitary or integral structure.

The overall specific gravity of the separator float 110 should be between that of red blood cells (approximately 1.090) and that of plasma (approximately 1.028). In a preferred embodiment, the specific gravity is in the range of from about 1.089-1.029, more preferably from about 1.070 to about 1.040, and most preferably about 1.05.

The float may be formed of multiple materials having different specific gravities, so long as the composite specific gravity of the float is within the desired range. The overall specific gravity of the float 110 and the volume of the annular gap 150 may be selected so that some red cells and/or plasma is retained within the annular gap, as well as the buffy coat layers. Upon centrifuging, the float 110 occupies the same axial position as the buffy coat layers and target cells, e.g., the float 110 resting on the packed red cell layer. The buffy coat is retained in the narrow annular gap 150 between the float 110 and the inner wall 136 of the tube 130. The expanded buffy coat region can then be examined, e.g., under illumination and magnification, to identify circulating epithelial cancer or tumor cells or other target analytes.

In one preferred embodiment, the density of the float 110 is selected to ride in the granulocyte layer of the blood sample. The granulocytes ride in, or just above, the packed red-cell layer and have a specific gravity of about 1.08-1.09. In this preferred embodiment, the specific gravity of the float is in this range of from about 1.08 to about 1.09 such that, upon centrifugation, the float rides in the granulocyte layer. The amount of granulocytes can vary from patient to patient by as much as a factor of about twenty. Therefore, selecting the float density such that the float rides in the granulocyte layer is especially advantageous since loss of any of the lymphocyte/monocyte layer, which rides just above the granulocyte layer, is avoided. During centrifugation, as the granulocyte layer increases in size, the float rides higher in the granulocytes and keeps the lymphocytes and monocytes at essentially the same position with respect to the float.

The method for detecting circulating epithelial cancer or stem cells in a blood of a subject disclosed in U.S. Pat. No. 6,197,523 may advantageously be modified to employ the sample tube and float system of the subject invention. The aforementioned U.S. Pat. No. 6,197,523 is incorporated herein by reference in its entirety.

In a preferred exemplary method of using the tube/float system 100 of the invention, a sample of anticoagulated blood is provided. For example, the blood to be analyzed may be drawn using a standard Vacutainer® or other like blood collection device of a type having an anticoagulant predisposed therein.

A fluorescently labeled antibody, which is specific to the target epithelial cells or other analytes of interest, can be added to the blood sample and incubated. In an exemplary embodiment, the epithelial cells are labeled with anti-epcam having a fluorescent tag attached to it. Anti-epcam binds to an epithelial cell-specific site that is not expected to be present in any other cell normally found in the blood stream. A stain or colorant, such as acridine orange, may also be added to the sample to cause the various cell types to assume differential coloration for ease of discerning the buffy coat layers under illumination and to highlight or clarify the morphology of epithelial cells during examination of the sample.

The blood is then transferred to the assembly 100 for centrifugation. The float 110 may be fitted into the tube 130 after the blood sample is introduced into the sample tube 130 or otherwise may be placed therein beforehand. The tube and float assembly 100 containing the sample is then centrifuged. Operations required for centrifuging the blood by means of the subject tube/float system 100 are not expressly different from the conventional case, although, as stated above, reduced centrifuge speeds may be possible and problems of slumping may be reduced. An adaptor may optionally be utilized in the rotor to prevent failure of the flexible tube due to stress.

When the centrifuging is started, the resultant hydrostatic pressure deforms or flexes the wall 136 so as to enlarge the diameter of the tube. The blood components and the float 110 are thus free to move under centrifugal motivation within the tube 130. The blood sample is separated into six distinct layers according to density, which are, from bottom to top: packed red blood cells, reticulocytes, granulocytes, lymphocytes/monocytes, platelets, and plasma. The epithelial cells sought to be imaged tend to also collect in the buffy coat layers, i.e., the granulocyte, lymphocyte/monocyte, and platelet layers as a result of their density. Due to the density of the float, it occupies the same axial position as the buffy coat layers and thus contents of the buffy coat occupy the narrow annular gap 150, potentially along with a small amount of the red cell and/or plasma layers).

After centrifugal separation is complete and the centrifugal force is removed, the tube 130 returns to its original diameter to capture or retain the buffy coat layers and other target analytes within the annular gap 150 for analysis. Optionally, the tube/float system 100 is transferred to a microscope or optical reader to identify any target cells in the blood sample.

Figure 3:
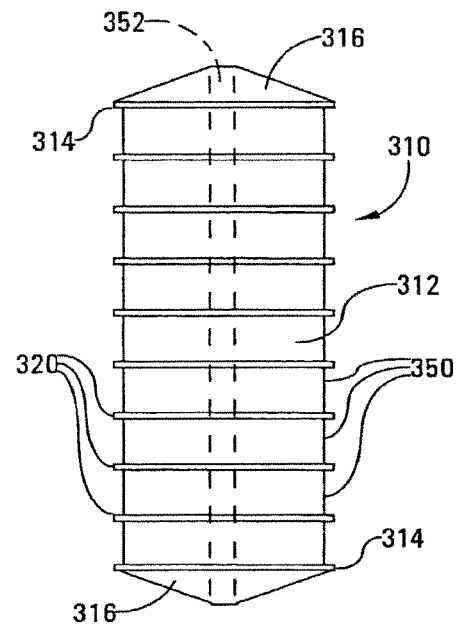
FIG. 3 is an elevational view of a separator float having axially spaced-apart ribs according to a further exemplary embodiment of the invention.

In one embodiment (see FIG. 3), the main body portion 312 has a diameter that is smaller than the inner diameter of the tube and, thus, multiple annular channels 350 are defined between the main body portion 312 and the inner tube wall. Optionally tapered ends 316 are provided to facilitate and direct the flow of cells past the float 310 and sealing ridges 314 during centrifugation. A central bore 352, shown in broken lines, provides a pressure relief outlet to alleviate any pressure build up in the lower fluid layers due to the contraction of the tube walls. Although the illustrated embodiment depicts continuous ribs, it will be recognized that the support ribs may likewise be broken or segmented to provide an enhanced flow path between adjacent annular channels 350.

Figure 4:
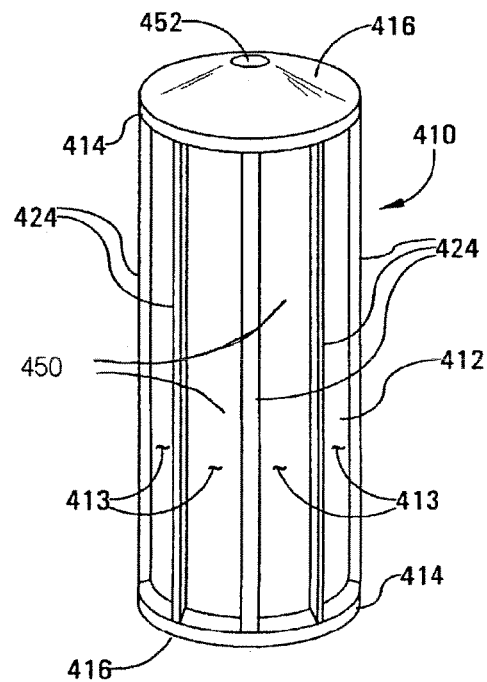
FIG. 4 is a perspective view of a separator float having axially extending ridges or splines according to yet another exemplary embodiment.

Referring now to FIG. 4, there is shown a splined separator float 410, including a plurality of axially oriented splines or ridges 424 which are radially spaced about a central body portion 412. End sealing ridges 414 and optionally tapered ends 416 are provided to facilitate and direct the flow of cells past the float 410 and sealing ridges 414 during centrifugation. The splines 424 and the end sealing ridges 414 protrude from the main body 412 to engage and provide support for the deformable tube once centrifugation is completed. The axial protrusions 424 define fluid retention channels 450, between the tube inner wall and the main body portion 412. The surfaces 413 of the main body portion disposed between the protrusions 424 may be curved, e.g., when the main body portion 412 is cylindrical, however, flat surfaces 413 are also contemplated. Although the illustrated embodiment depicts splines 424 that are continuous along the entire axial length of the float 410, segmented or discontinuous splines are also contemplated. A pressure relief bore 452 extends axially and centrally through the float 410. In other embodiments, one or more of such pressure relief bores, of similar or different shape, can be included in the main body of the float.

Figure 5:
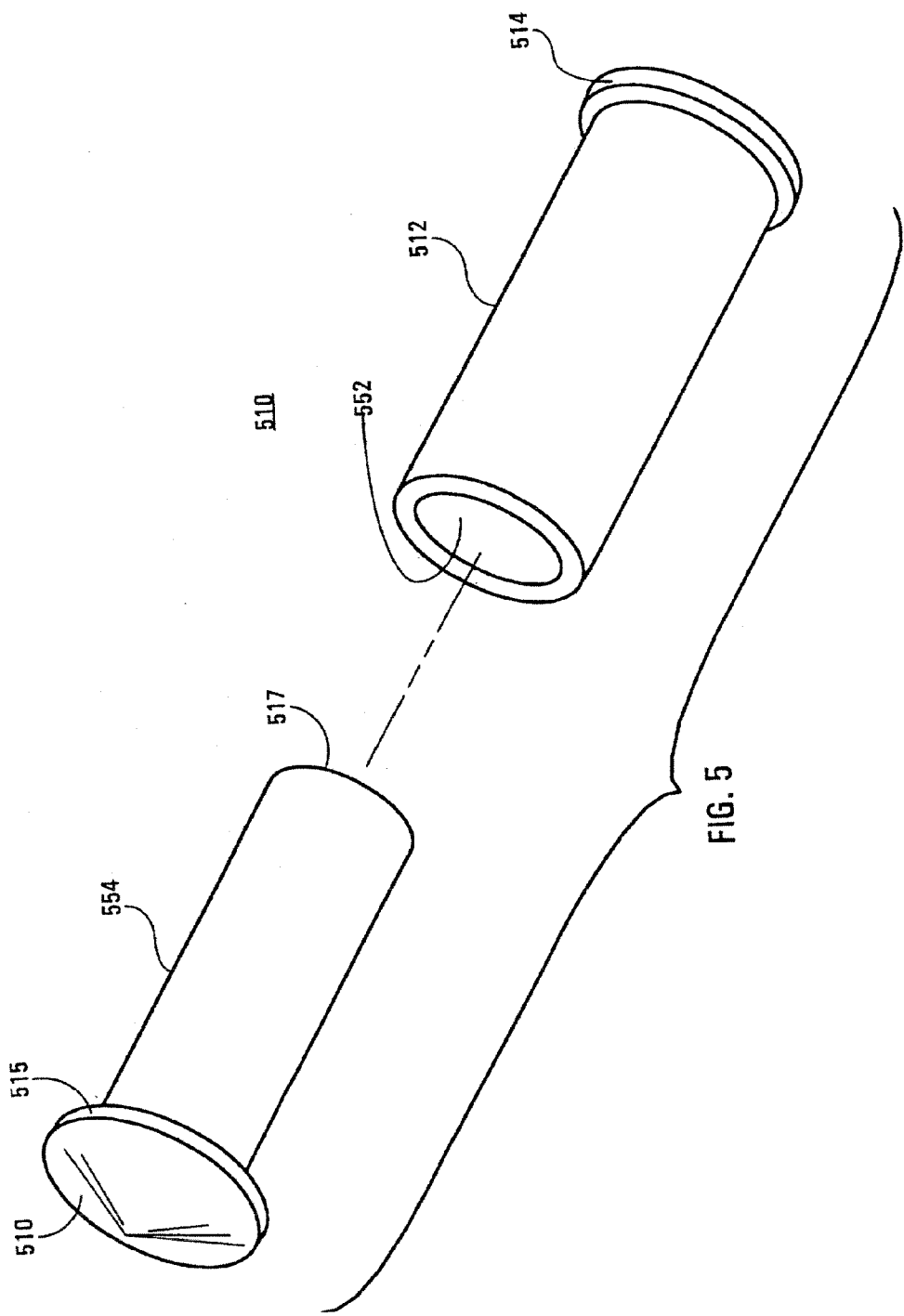
FIG. 5 is an exploded perspective view of a two-piece separator float according to still another exemplary embodiment of the invention.

FIG. 5 illustrates a two-piece float 510 in accordance with a preferred embodiment of the present invention, shown in exploded view. A first, main body portion or sleeve 512 includes a central bore 552, which is sized to slidably receive a second, piston-like center portion 554. The outer body member 512 includes a flange or sealing ring 514, which is at its lower or bottom end. A sealing ridge or flange 515 is disposed at the upper end of the piston section 554 during operation. Optionally tapered ends 517 are preferably provided at the upper and lower (during operation) ends of the piston portion 554 to facilitate and direct the flow of cells past the sealing ridges 514 and 515 during centrifugation.

The difference between the diameter of the main body 512 and the diameters of the sealing rings 514 and 515 are as described above by way of reference to FIG. 1. In operation, the piston portion 554 is fully received within the central bore 552 of the main body member 512. As stated above, the float 510 is oriented in the tube so that the sealing ridge 515 is at the top and the sealing ridge 514 is toward the bottom of the tube. The two portions may be formed of the same material or different materials, so long as the overall specific gravity of the float 510 is in a suitable range for buffy coat capture. In an especially preferred embodiment, the central piston portion 554 is formed of a slightly higher specific gravity material than the outer portion 512, which insures that the two portions stay together during centrifugation. Alternatively, the two float members are formed of the same material and/or a frictional fit sufficient to keep the float members together during centrifugation is provided.

As the tube containing the blood sample and float 510 is centrifuged, the two pieces 512 and 554 stay together and act in the same manner as a one-piece float to axially expand the buffy coat layers. When separation and layering of the blood components is complete and centrifugation is slowed, pressure may build in the red blood cell fraction trapped below the float, e.g., where contraction of the tube continues after initial capture of the float by the tube wall. Any such pressure in the trapped red blood cell region forces the center piece 554 upward, thus relieving the pressure, and thereby preventing the red blood cells from breeching the seal between the sealing rings 514 and the tube wall.

FIGS. 6-12 illustrate further two-piece float embodiments of the present invention wherein the sealing rings are disposed at each end of the outer sleeve and pressure relief is provided by an upwardly movable piston member.

Figure 6:
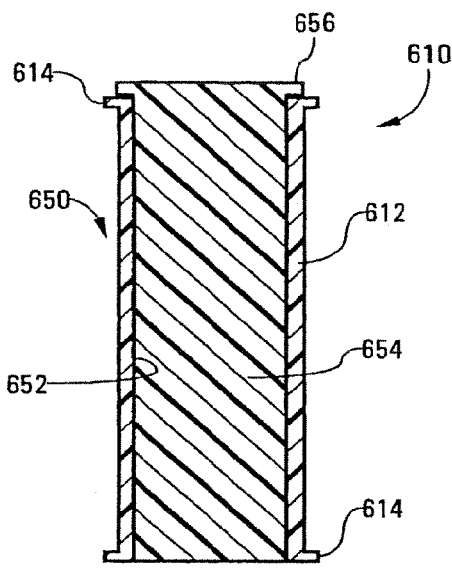
FIGS. 6-12 are side sectional views of additional exemplary two-piece float embodiments of the invention.

FIG. 6 illustrates a two-piece float 610 including a first, main body portion or sleeve 612 having a central bore 652 slidably receiving a second, piston-like center portion 654. The outer body member 612 includes a sealing ring or ridge 614 at each end sized to engage the tube 130 (FIG. 1), with an annular recess 650 defined therebetween. The piston 654 includes a flanged end 656 that is greater in diameter than the central bore 652 and less than the diameter of the sealing ridges 614.

In operation, the piston member 654 is fully received within the central bore 652, with the flange 656 abutting the upper end of the sleeve 612. In use, the float 610 is oriented in the tube so that the flange 656 is located toward the top of the tube 130, i.e., toward the stopper 140 (FIG. 1). Again, the two portions may be formed of the same material or different materials, so long as the overall specific gravity of the float 610 is in a suitable range for buffy coat capture. In an especially preferred embodiment, the central portion 654 is formed of a slightly higher specific gravity material than the outer portion 612, which insures that the two portions stay together during centrifugation. Alternatively or additionally, a frictional fit is provided between the two float sections. Upon completion of centrifugation, any pressure build up in the trapped red blood cell region is alleviated by forcing the center piece 654 upwardly.

Figure 7:
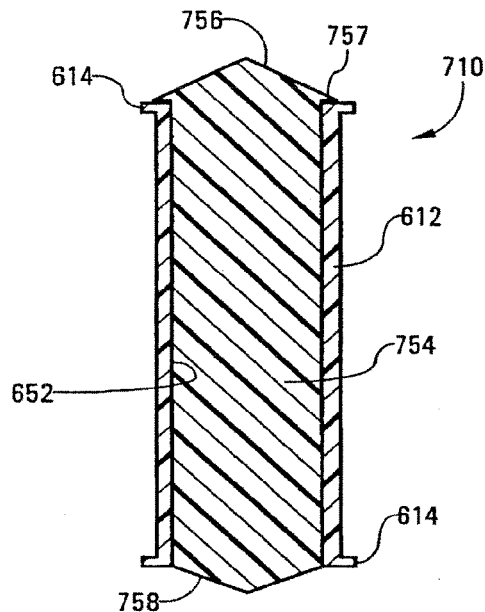

FIG. 7 illustrates a two-piece float 710 similar to that shown and described by way of reference to FIG. 6, but further including tapered ends for facilitating blood flow around float 710 during centrifugation. A first, main body portion or sleeve 612 has a central bore 652 slidably receiving a second, piston-like center portion 754. The outer body member 612 includes sealing rings or ridges 614 at opposite ends, as described above. The piston 754 includes a tapered end 756 including a flange 757 sized to abut the sleeve 612 upon insertion and restrict any further downward passage of the piston 754. A lower end 758 of the piston member 754 is also tapered to facilitate flow. Centrifugal motivation and/or a frictional fit may be used to insure the two sections remain together during centrifugation.

Figure 8:
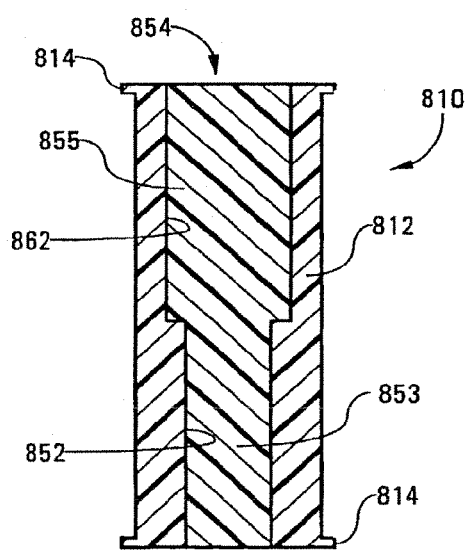

FIG. 8 illustrates a two-piece float 810 including a first, main body portion or sleeve 812 having a central bore 852 and a counterbore 862, slidably receiving a second, piston-like center portion 854. The outer body member 812 includes a sealing ring or ridge 814 as described above. The piston 854 includes a first, smaller diameter portion sized to be received within the central bore 852 and a second, larger diameter portion sized to be received within the counterbore 862. The axial extent of the small diameter segment 853 and large diameter segment 855 may vary widely and are complimentary to that of the bore 852 and counterbore 862, respectively.

Figure 9:
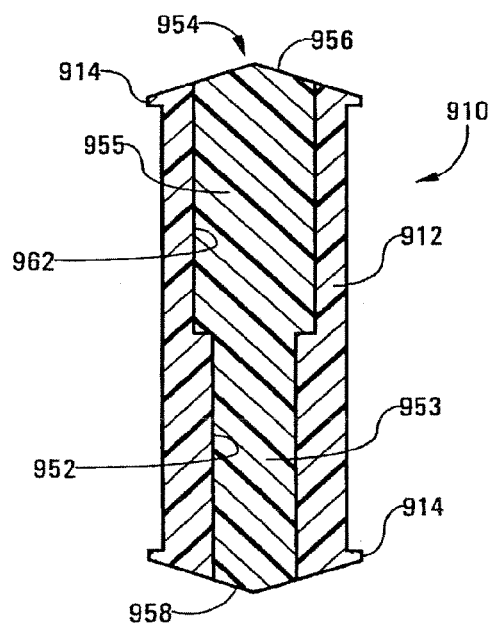

Although the float 810 is shown with generally flat ends, it will be recognized that the ends of the piston member 854 and/or sleeve member 812 may be tapered to facilitate fluid flow around the float during centrifugation. FIG. 9 illustrates an embodiment similar to that shown in FIG. 8, having tapered ends. A two-piece float 910 includes a first, main body portion or sleeve 912 having a central bore 952 and a counterbore 962, slidably receiving a second, piston-like center portion 954. The outer body member 912 includes a sealing ring or ridge 914. The piston 954 includes a first, smaller diameter portion sized to be received within the central bore 952 and a second, larger diameter portion sized to be received within the counterbore 962. The tapered ends 956 and 958 cooperate with complimentary end ridges to form generally conical ends.

Referring to FIGS. 8 and 9, during centrifugation, the float (810; 910) is oriented in the tube so that the counterbore and larger diameter portion are located toward the top of the tube 130 (FIG. 1). As described above, the two portions may be formed of the same material or different materials and, in the preferred embodiment, the central portion (854; 954) is formed of a slightly higher specific gravity material than the outer sleeve (812; 912) insuring that the two sections stay together during centrifugation. Upon completion of centrifugation, any pressure built up in the trapped red blood cell region forces the center section (854; 954) upwardly.

Figure 10:
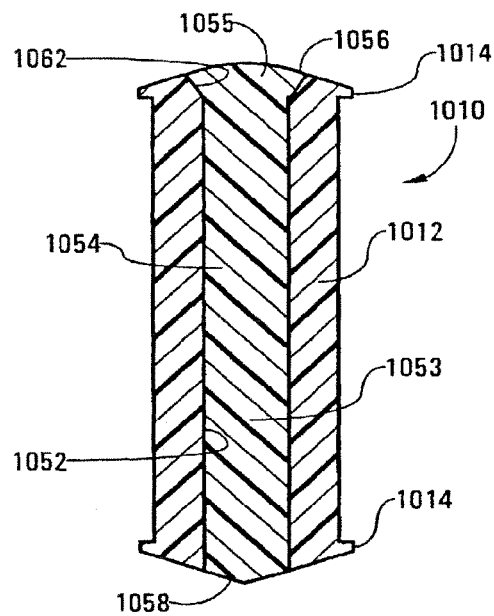

FIG. 10 illustrates yet another two-piece float embodiment 1010 including a first, main body portion or sleeve 1012 having a profiled bore comprising a central bore 1052 and an enlargement or countersink 1062 opening toward the upper end of the tube. A second, piston-like movable member 1054 includes a shaft 1053 and an enlarged head 1055, which are complimentary to and slidably received in the central bore 1052 and the countersink 1062, respectively. The outer sleeve 1012 includes sealing rings or ridges 1014 as described above. The float 1010 is shown with tapered ends 1056 and 1058, however, it will be recognized that the ends of the float

1010 may also be flat. As described above, the two sections 1012 and 1054 may be formed of the same material or different materials and, in the preferred embodiment, the movable member 1054 is formed of a slightly higher specific gravity material than the outer sleeve 1012, insuring that the two sections stay together during centrifugation.

Figure 11:
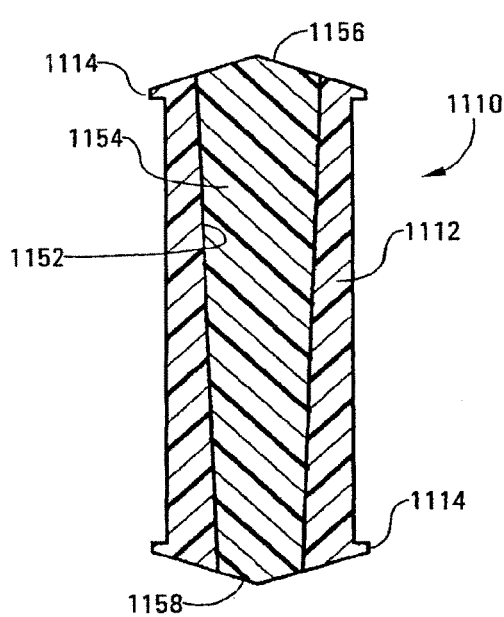

FIG. 11 illustrates a further two-piece separator float embodiment 1110 including a first, main body portion or sleeve 1112 having a tapered internal passage 1152 which widens toward the upper end 1156 of the float. A central, movable member 1154 complimentary to the bore 1152 is slidably received therein. The outer sleeve 1112 includes sealing rings or ridges 1114. The separator float ends 1156 and 1158 are illustrated as tapered, although flat ends are also contemplated. The two sections 1112 and 1154 may be formed of the same material or different materials, again, with the movable member 1154 preferably formed of a slightly higher specific gravity material to keep the float sections together during centrifugation.

Figure 12:
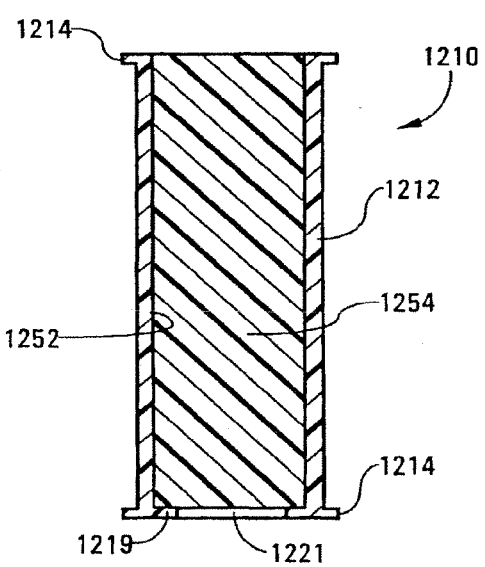

FIG. 12 illustrates a further two-piece separator float embodiment 1210 including a first, main body portion or sleeve 1212 having an central passage or bore 1252 which terminates in an annular seat 1219 formed at a lower end of the float 1210 and defining an opening 1221 into the bore 1252. A piston-like movable member 1254 is slidably received within the bore 1252, abutting the annular seat 1219. The outer sleeve 1212 includes sealing rings or ridges 1214. The separator float 1210 is depicted with flat ends, although tapered ends are also contemplated. Optionally, the movable member 1254 may contain a narrow diameter portion (not shown) on the lower end thereof sized to be received in the aperture 1221, e.g., to provide a flush and/or tapered surface to facilitate flow therepast during centrifugation. The two sections 1112 and 1254 may be formed of the same material or different materials; preferably, the movable member 1254 is formed of a slightly higher specific gravity material to keep the float sections together during centrifugation.

Each of the float embodiments of FIGS. 1, 2, and 6-12, which have been illustrated with end sealing rings and without additional tube supporting members for ease of demonstration, may be further modified by the further incorporation of any of the tube support features as shown and/or described in the above-incorporated U.S. patent application Ser. No. 10/263,975, now U.S. Pat. No. 7,074,577, such as annular bands, segmented bands, helical bands, axial splines, rounded protrusions, spikes, facets, and combinations thereof. Likewise, the separator float embodiments are depicted herein having either flat or the preferred conical ends; however, many other geometrical shapes providing a curved, sloping, and/or tapered surface to facilitate density-motivated cell and float movement during centrifugation are contemplated, such as those shown and/or described in the above-incorporated U.S. patent application Ser. No. 10/263,975, now U.S. Pat. No. 7,074,577. Exemplary modified end shapes include, for example, frustoconical, convex or dome-shaped, and other tapered shapes.

In use, a tube adapter may be used which insures sufficient expansion of the flexible tube to facilitate free movement of the separator float while not allowing the tube to overexpand, which may lead to tube failure, e.g., breakage or plastic deformation of the tube. Therefore, a tubing adapter retaining the tube having an inner diameter sized to provide a specific clearance gap between the adapter and the outer diameter of the tube is advantageously used during centrifugation. This gap limits the expansion of the tube to a sufficient amount to allow the float to move freely in the tube, but not so much as to allow the tube to fail.

Although suitable tubes are commercially available, an exemplary, preferred method for manufacturing the tubes addresses performance attributes necessary to maintain and visualize the buffy coat. First, it has been found that imperfections in the test tube provide wicking paths for red blood cells to intrude on the separated buffy coat retained in the annular gap. Typically, the most severe imperfection found on the commercially available test tubes is the molding parting line running the length of the test tube. Therefore, a sample tube was developed with the parting line at the bottom of the tube where it does not interfere with the dynamics of the tube/float/blood interaction. Since this process requires pulling the tubes from the injection mold rather than splitting the mold, which produces the parting line, the top of the test-tube may be thickened and flared out to facilitate using a stripper plate to remove the tubes. Other known methods for forming seamless tubing may be employed as well.

In addition, the mold used consisted of a long core for the center of the sample tube. During molding, the pressure of the injection process tends to deform the core, producing uneven tube thicknesses. A feature from the main part of the mold was, therefore, added that mates with the free-end of the core, the feature being the injector of the plastic. The mating action fixes the core to prevent deflection during injection. Late in the injection process, during injection, the feature is withdrawn and plastic fills the remainder of the tube.

Efficient methods for manufacturing the floats have also been developed. In the case of the one-piece floats, injection molding is difficult because the thickness of the float makes it difficult to control the shrinkage of the plastic part, the amount of shrinkage being proportional to the thickness of the part. Some of this concern is addressed in the case of the two-piece floats by virtue of the fact two thinner parts that can be molded separately. That is, the thickness of these parts can be kept below about one-half inch, which typically defines the thickness limit for accurate molding. If further accuracy on any particular part, especially the outer dimension of the one-piece or two-piece floats, "over molding" can be employed. In this process, the part is molded in two steps. The first step molds most of the part smaller than desired, leaving a thin layer to be added later. The shrinkage of the thin layer which is molded on in the second step can be more precisely controlled, thus allowing a more precisely dimensioned part to be molded.

Once the buffy layer is separated, it is desirable to present the tube to an automated inspection system for imaging and analysis. This requires precise positioning of the tube. Therefore, features may be added to the sample tube, e.g., to the bottom of the tube, to facilitate tube engagement, handling, and positioning, e.g., under automated or preprogrammed control.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A volume occupying separator float for use with an associated sample tube, comprising:
   a main body portion having a top axial end and a bottom axial end;
   a continuous top sealing ridge protruding radially from the top axial end of the main body portion;
   a continuous bottom sealing ridge protruding radially from the bottom axial end of the main body portion; and an internal passage extending axially completely through the main body portion, bottom sealing ridge, and top sealing ridge;

wherein the main body portion tapers from the top axial end towards the top sealing ridge and from the bottom axial end towards the bottom sealing ridge.

2. The volume occupying separator float of claim 1, wherein the float has a height of 3.5 centimeters and a diameter of 1.5 centimeters.

3. The volume occupying separator float of claim 1, wherein the float has a specific gravity of from about 1.028 to about 1.090.

4. The volume occupying separator float of claim 1, wherein the float has a specific gravity of from about 1.08 to about 1.09.

5. The volume occupying separator float of claim 1, wherein the internal passage has a greater cross-sectional area at the top axial end than at the bottom axial end.

6. The volume occupying separator float of claim 1, further comprising a plurality of ribs protruding radially from the main body portion, the ribs being located between the top sealing ridge and the bottom sealing ridge.

7. A volume occupying separator float for use with an associated sample tube for centrifugation, comprising:

a rigid main body portion having a top axial end and a bottom axial end;

a top sealing ridge protruding radially from the top axial end of the main body portion;

a bottom sealing ridge protruding radially from the bottom axial end of the main body portion; and an internal passage extending axially completely through said main body portion;

wherein the main body portion tapers from the top axial end towards the top sealing ridge and from the bottom axial end towards the bottom sealing ridge; and wherein the top sealing ridge and the bottom sealing ridge protrude an equal distance from the main body portion.

8. The volume occupying separator float of claim 7, wherein the float has a height of 3.5 centimeters and a diameter of 1.5 centimeters.

9. The volume occupying separator float of claim 7, wherein the float has a specific gravity of from about 1.028 to about 1.090.

10. The volume occupying separator float of claim 7, wherein the float has a specific gravity of from about 1.08 to about 1.09.

11. The volume occupying separator float of claim 7, wherein the internal passage has a greater cross-sectional area at the top axial end than at the bottom axial end.

12. The volume occupying separator float of claim 7, wherein the main body portion, top sealing ridge, and bottom sealing ridge form a unitary structure.

13. The volume occupying separator float of claim 7, wherein the top and bottom sealing ridges both protrude from the main body portion to form continuous surfaces.

14. The volume occupying separator float of claim 7, wherein the main body portion tapers towards the top and bottom sealing ridges so as to form a curved surface at the top axial end and the bottom axial end.

15. The volume occupying separator float of claim 7, wherein the main body portion tapers towards the top and bottom sealing ridges so as to form a sloped surface at the top axial end and the bottom axial end.

16. The volume occupying separator float of claim 7, wherein the top axial end and the bottom axial end are conical.

17. The volume occupying separator float of claim 7, further comprising a plurality of ribs protruding radially from the main body portion, the ribs being located between the top sealing ridge and the bottom sealing ridge.

18. The volume occupying separator float of claim 17, wherein the plurality of ribs protrude the same distance from the main body portion as the top and bottom sealing ridges.

19. The volume occupying separator float of claim 17, wherein the ribs are spaced equally apart.

20. The volume occupying separator float of claim 17, wherein there are a total of 8 ribs.

\* \* \* \* \*